US00PP31404P3

(12) United States Plant Patent
Infante Espiñeira

(10) Patent No.: US PP31,404 P3
(45) Date of Patent: Jan. 28, 2020

(54) ASIAN PLUM TREE NAMED 'SWEET PEKEETAH'

(50) Latin Name: *Prunus salicina*
Varietal Denomination: Sweet Pekeetah

(71) Applicant: UNIVERSIDAD DE CHILE, Santiago (CL)

(72) Inventor: Rodrigo Arturo Infante Espiñeira, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 15/732,605

(22) Filed: Dec. 1, 2017

(65) Prior Publication Data

US 2018/0160583 P1 Jun. 7, 2018

(30) Foreign Application Priority Data

Dec. 6, 2016 (CL) ..... 1664

(51) Int. Cl.
*A01H 5/08* (2018.01)
*A01H 6/74* (2018.01)

(52) U.S. Cl.
USPC ..... Plt./184
CPC ..... *A01H 6/7472* (2018.05); *A01H 5/08* (2013.01)

(58) Field of Classification Search
USPC ..... Plt./184
CPC ..... A01H 5/0862; A01H 5/0837
See application file for complete search history.

*Primary Examiner* — Kent L Bell
(74) *Attorney, Agent, or Firm* — Merchant & Gould P.C.

(57) ABSTRACT

A new and distinct plum variety is described. 'Sweet Pekeetah' is an Asian plum variety with unique traits, as extremely late blooming and ripening dates. The flesh of 'Sweet Pekeetah' has crunchy texture, green color and soluble solids concentration reaches 20-22%, with upstanding sensory quality. The postharvest life potential of 'Sweet Pekeetah' can last 60 days keeping the original high sensory quality.

3 Drawing Sheets

BACKGROUND

Seedlings obtained from collecting seed from open pollinated fruit during controlled hybridization. This new cultivar resulted from a controlled hybridization between the Asian plum genotype known as '213-UR-056' (female progenitor) and the Asian plum genotype '178-R-01' (Male progenitor). Both progenitors are non-patented genotypes that are currently used as recurrent parental in the breeding program of the University of Chile. The sexual crossing was performed in 2008 at Rinconada de Maipú, Metropolitan Region, Chile (latitude −33° 30'S, longitude −70° 48'W, altitude 654 m above sea level). This genotype was for the first time asexually propagated through grafting on 'Nemaguard' rootstock in the same field on 2011. The rootstock 'Nemaguard' is a chance seedling selected in 1959 by USDA, and it has never been patented. The invention described herein relates to the discovery and the asexual propagation through grafting on 'Nemaguard' rootstock of a new variety of Asian plum tree, *Prunus salicina* named 'Sweet Pekeetah'. The resulting plants propagated true to type, demonstrating that the characteristics of the new variety are stable and transmitted without change through succeeding generations.

SUMMARY

The main differences between "Sweet Pekeetah" and its progenitors '213-UR-056' (female progenitor) and '178-R-01' (Male progenitor), is that "Sweet Pekeetah" blooms 20 days after '213-UR-056' and 10 days before '178-R-01'. The fruit of "Sweet Pekeetah" reaches 150 g, while neither of its progenitors reaches more than 100 g. Under the Chilean growing conditions 'Sweet Pekeetah' is distinguished from varieties of common knowledge such as 'Angeleno' and 'Friar' by the following characteristics:

The ripening period of 'Angeleno' is three to four weeks before that of the 'Sweet Pekeetah'. Additionally, the fruit of 'Sweet Pekeetah' has higher soluble solids concentration and lower softening rate than the variety 'Angeleno'. Compared with 'Angeleno', 'Sweet Pekeetah' shows a firmer and more crunchy flesh, the fruit size is 140-150 gr. 'Angeleno' plum is harvested in Chile on approximately February 20$^{th}$ and 'Sweet Pekeetah' is harvested 15 to 20 days after.

The fruit of 'Friar' are moderately asymmetric and the shape of apex is depressed, conversely the fruit of 'Sweet Pekeetah' are symmetric and the shape of apex is rounded. The color of flesh of 'Friar' is yellow and the color of flesh of 'Sweet Pekeetah' is yellowish green. 'Friar' plum is harvested in Chile on approximately January 20$^{th}$, and 'Sweet Pekeetah' is harvested 35 to 40 days after.

DETAILED DESCRIPTION

Figure 1:
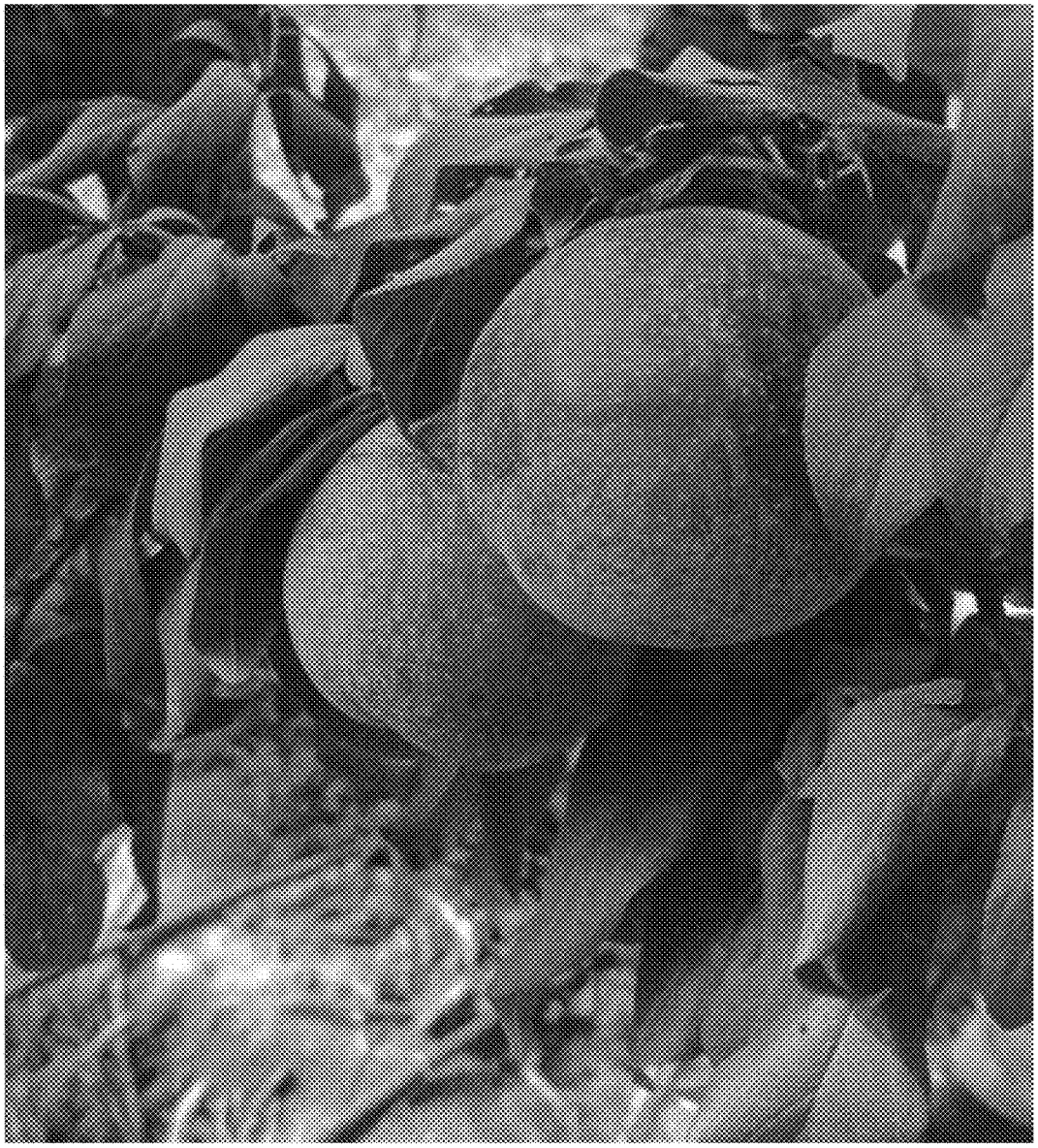
FIG. 1 is a photograph showing a typical specimen of the foliage and fruit of the new variety depicted in colors as nearly true as is reasonably possible to make the same in a color illustration of this character. The observations were made on mature trees which ranged in age between four and five years old, four years after budding. The photograph shows the 'Sweet Pekeetah' fruit just after harvest.
Figure 2:
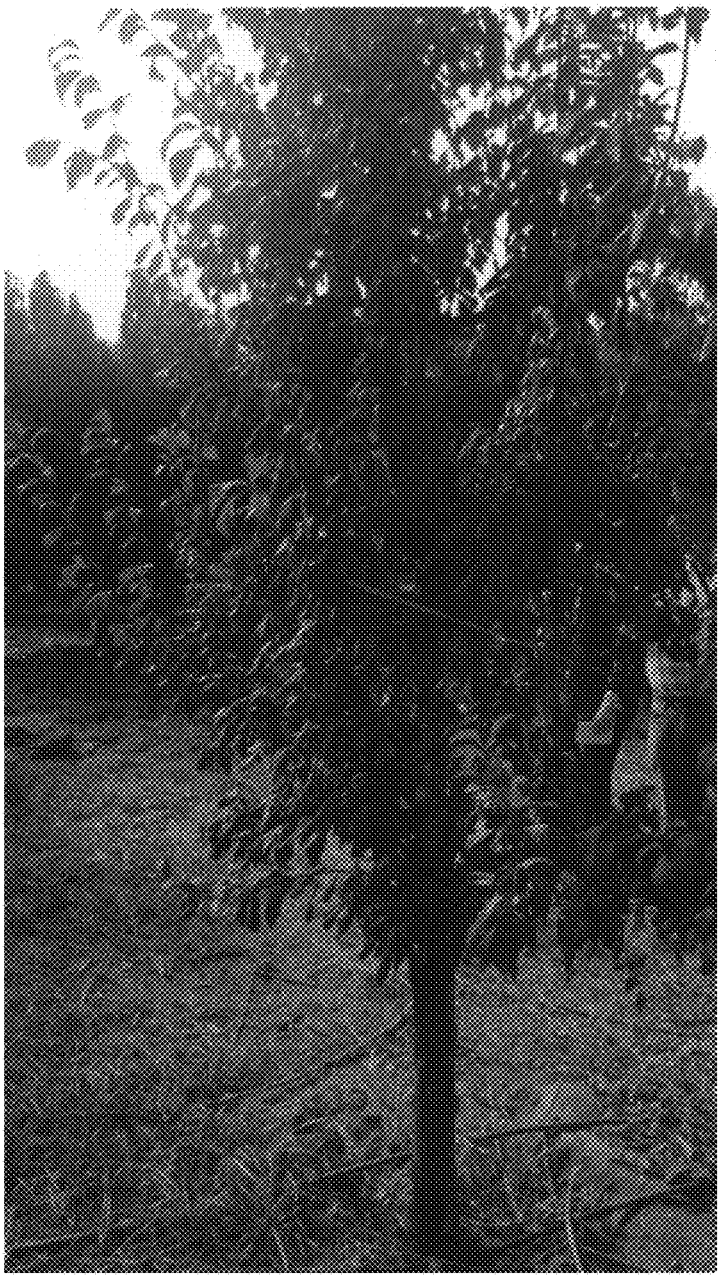
FIG. 2 shows a tree of 'Sweet Pekeetah', with height, foliage and fruit of the new variety depicted in colors as nearly true as is reasonably possible to make the same in a color illustration of this character.
Figure 3:
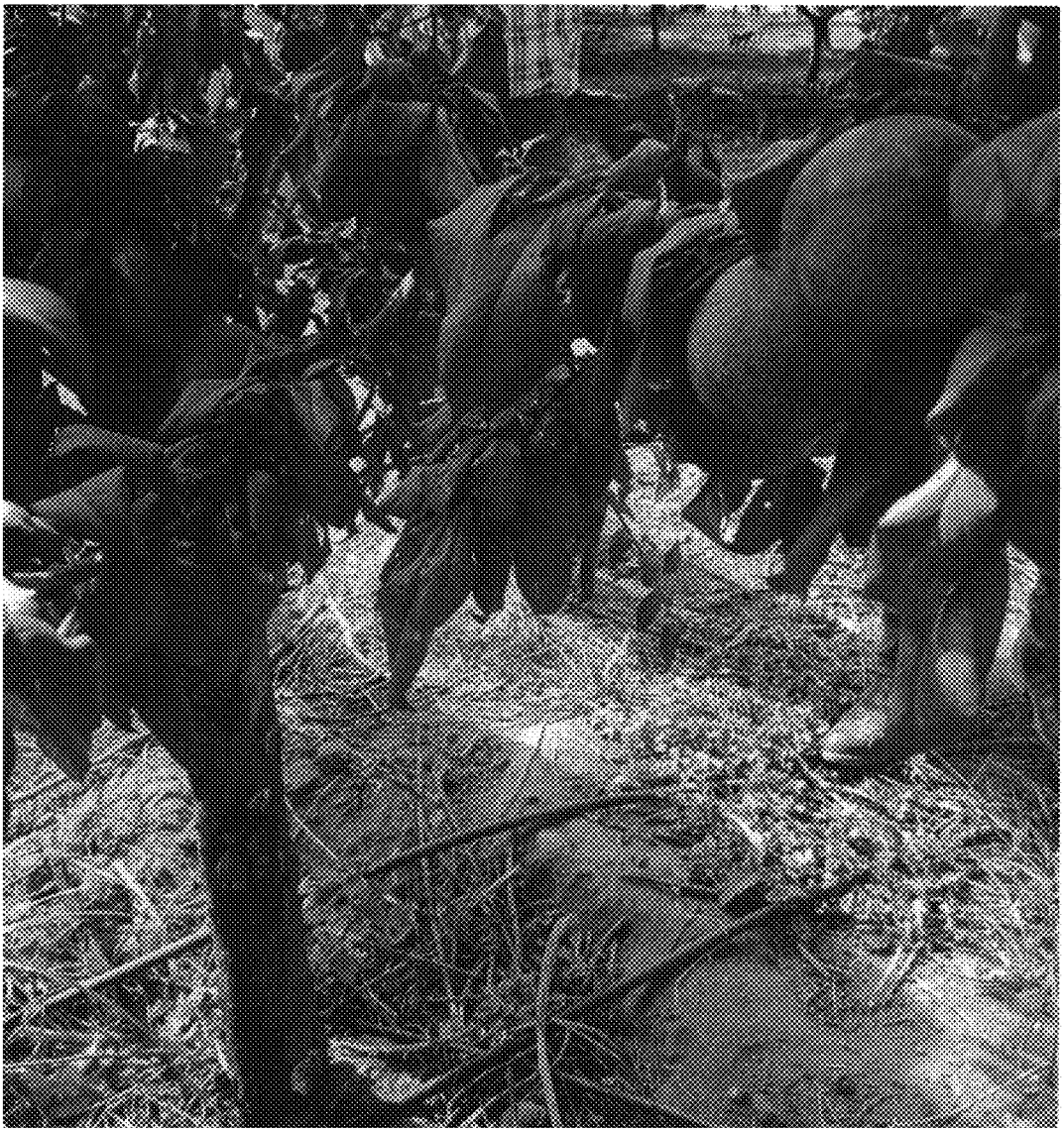
FIG. 3 shows a branch of 'Sweet Pekeetah' tree showing fruits and leaves as nearly true as is reasonably possible to make the same in a color illustration of this character.

The 'Sweet Pekeetah' is a self-unfertile, with semi erect plant growth, weak to medium vigor. The fruit is round, symmetrical, with a deep purple skin color that covers 80 to 90% of the surface over a green background color.

Blooming time of 'Sweet Pekeetah' is extremely late, being contemporary to some European plums as 'French prune', which is three to four weeks after the majority of known Asian plum varieties.

The main feature of 'Sweet Pekeetah' is its slow pulp softening rate commencing during the last two weeks before the commercial harvest. This characteristic enables delaying the harvest, to increase the size of the fruit and the soluble solids content without affecting their post-harvest life potential.

Secondly, 'Sweet Pekeetah' shows a high post-harvest life, which can reach up to 60 days at 0° C. while maintaining its initial sensory quality. From a sensory point of view, this is a variety of medium acidity with a balanced sweetness/acidity ratio and in general an upstanding sensory quality. The variety is not susceptible to "chilling injury" and therefore can be suitable for exporting to distant markets from the production zone. Another distinguishing factor compared to other known varieties is that the 'Sweet Pekeetah' reaches a high soluble solid concentration, which can scores 20 to 22%, while 'Angeleno', for example, barely reaches 16%.

The flesh of 'Sweet Pekeetah' when picked shows a brilliant green color, which is also a remarkable and not common characteristic among this species. The green color of the flesh remains for the first 20 days when fruit is maintained in cold chamber, but after that period, it began to change to yellow-orange. In term of texture, 'Sweet Pekeetah' has an uncommon crunchiness at harvest and even after 60 days of cold storage.

The following is a brief description of the new variety with color terminology in accordance with CIELab coordinates.

The observations were made on mature trees which ranged in age between four and five years old. Trees were grown under standard orchard practices.

Bearer: Regular, showed adequate fruit set in 10 consecutive years. No alternate bearing has been observed.

Hardiness zone: Hardy in all stone fruit growing areas of Central Chile which is similar to California. Tree should grow in USDA Hardiness Zone 9.

Disease and pest resistance: Similar to "Angeleno", showing no special resistance to any disease or pest.

Chilling requirements: Winter chilling requirement approximately 550-600 hours at or below 0° C. (45° F.).

Tree: Medium size, reaching 3.5-3.9 m high shaped as an open vase, 2.0-2.2 m diameter at the fifth year e, reaching 3 to 3.5 meters in height in mature trees.

Type of bearing: On spurs and long shoots, similar to cultivar 'Angeleno' and 'Shiro'.

Vigor: Weak, similar to cultivar 'Black Gold' and 'Satsuma', shoots reach 40 to 60 cm and shoot thickness reach 4.5-5.0 mm diameter on a regular spring/summer growing period.

Trunk: Medium in size, average circumference 52.0 cm at 20.0 cm above ground on an 8 year old tree. The texture is medium shaggy, and the color L=22.80 a=3.75 b=8.22 (Mcguire R. G., 1992).

Habit: Semi-upright, similar to cultivar 'Laroda'. The size of the tree is medium, reaching 3.5-3.9 m high shaped as an open vase, 2.0-2.2 m diameter at the fifth year.

One-year-old shoot, color: Brown, similar to cultivar 'Methley', the objective color in CIELab coordinates is L=26.40 a=3.37 b=7.51 (Mcguire R. G., 1992).

Mature branch: Medium, with an average circumference 15.4 cm at 1.0 meter above ground and its crotch angle is large, approximately 60°. The surface texture is smooth when young and tend to be rough when mature. The color is L=22.17 a=3.70 b=8.22 (Mcguire R. G., 1992).

Spur length: Medium, similar to cultivar 'Frontier' and the flowering shoot thickness reach 3.0-5.3 cm diameter and 8-10 cm length. The objective color in CIELab coordinates is L=26.00 a=3.92 b=7.77 (Mcguire R. G., 1992).

Vegetative bud: Size: Small, similar to cultivar 'Harry Pickstone', reaching 5-7 mm length.

Vegetative bud: shape of apex: Acute, similar to cultivar 'Eldorado'.

One-year-old shoot position of vegetative bud in relation to shoot: Adpressed, similar to cultivar 'Queen Ann'.

Leaf base: Cuneate.

Leaf blade length: Medium, reaching 12.8 cm length, similar to cultivar 'Taiyou'.

Leaf blade width: Medium, reaching 5.5 cm width, similar to cultivar 'Sordum'.

Leaf blade, length/width ratio: Moderately elongated, reaching in average 2.3, similar to cultivar 'Pioneer'.

Leaf blade shape: Elliptic, similar to cultivar 'Black Gold' and 'Taiyou'.

Leaf blade color of upper side: Medium green, like cultivar 'Abundance', classified in CIELab coordinates: L=37.45 a=−8.20 b=−15.48 (Mcguire R. G., 1992).

Leaf blade under surface: Pale green, like cultivar 'Shiro', classified in CIELab coordinates: L=32.65 a=−7.10 b=−14.80 (Mcguire R. G., 1992).

Leaf blade angle of apex (excluding tip): Acute, like cultivar 'Taiyou'.

Leaf glossiness of upper side: Medium, similar to cultivar 'Frontier'.

Leaf blade density of pubescence of lower side: Sparse, similar to cultivar 'Angeleno'.

Leaf blade incisions of margin: Serrate, like cultivar 'Dapple Dandy'.

Petiole length: Medium, similar to cultivar 'Frontier', reaching 1.3 cm length, and 0.1 cm diameter. The color is green, classified in CIELab coordinates: L=37.15 a=−7.97 b=−15.19 (Mcguire R. G., 1992).

Leaf position of nectaries: Predominantly on base of leaf blade, like cultivar 'Methley'.

Pedicel length: Medium, reaching approximately 10 mm length, similar to cultivar 'Queen Ann', and 0.2 cm diameter. The color is green, classified in CIELab coordinates: L=37.01 a=−7.63 b=−15.00 (Mcguire R. G., 1992).

Flower:

Buds: Medium size, average length 1.0 cm, and average diameter 0.5 cm. The form is conical.

Height: The flower is round shaped and 2.5-2.8 cm height.

Diameter: Medium, reaching 15-17 mm, like cultivar 'Shiro'.

Arrangement of petals: Free, similar to cultivar 'Laroda'.
Sepal shape: Narrow elliptic, similar to cultivar 'Laroda'.
Sepal: Number normally 5, alternately arranged to petals. The sepal apex is triangular and the size is medium. Average length 4.0 mm. Average width 2.5 mm. Triangular shape. The margin is entire. The upper and the lower surfaces are glabrous. The color is green, classified in CIELab coordinates: L=38.14 a=−10.96 b=14.88 (Mcguire R. G., 1992).
Petals: Number: normally 5, alternately arranged to sepals. Petal apex is rounded and the petal base is truncate. The form is globose to elliptical. The petal margin is sinuate. The color is white, classified in CIELab coordinates: L=87.14 a=−0.45 b=5.78 (Mcguire R. G., 1992).
Petal length: The size is medium. Average length 1.0 cm, and the average width 0.7 cm like cultivar 'Santa Rosa'.
Petal shape: Obovate, similar to cultivar 'Mammoth Cardinal'.
Petal undulation of margin: Medium, like cultivar 'Queen Ann'.
Stigma position in relation to anthers: Below, similar to cultivar 'Mariposa'.
Reproductive organs:
Stamens: Average number per flower 20. Average filament length 5.5 mm. On average the stamens are below the height of the petals. Filament color is white, classified in CIELab coordinates: L=97.38 a=−0.42 b=3.18 (Mcguire R. G., 1992).
Anther color: Is yellow, classified in CIELab coordinates: L=76.05 a=6.94 b=43.55 (Mcguire R. G., 1992).
Pollen: Self sterile, pollinator required. Color is yellow, classified in CIELab coordinates: L=78.58 a=2.26 b=31.58 (Mcguire R. G., 1992).
Pistil number: Normally 1. Surface glabrous. Average length 8.0 mm. Position of stigma an average of 1.5 mm below anthers. Color is pale green, classified in CIELab coordinates: L=84.14 a=−7.38 b=18.65 (Mcguire R. G., 1992).
Fragrance: Present.
Pedicel: Average length 5.0 mm. Average width 0.7 mm. The color is pale green, classified in CIELab coordinates: L:41.09 a:−11.45 b:16.94.
Number flowers per flower bud: Average number 3, varies from 2 to 4.
Fruit:
Length of stalk: Medium, reaching in average 8.9 mm, similar to cultivar 'Sordum'. The color is light green, classified in CIELab coordinates: L=38.11 a=−7.07 b=−15.98 (Mcguire R. G., 1992).
Size: Medium, like cultivar 'Shiro', reaching 140-150 gr.
Height: Medium, reaching in average 55.4 mm similar to cultivar 'Harry Picktone'.
Width: Medium, diameter in line with suture plane, approximately 60 mm. Diameter perpendicular to suture plane 65 mm, similar to cultivar 'Casselman'.
Shape in lateral view: Oblate, similar to cultivar 'Friar'.
Symmetry: Slightly asymmetric, like cultivar 'Laroda'.
Shape of base: Depressed, similar to cultivar 'Calita'.
Shape of apex: Rounded, similar to cultivar 'Shiro'.
Depth of stalk cavity: Medium, reaching in average 9.0 mm, like cultivar 'Angeleno'.
Width of stalk cavity: Medium, reaching approximately 12 mm similar to cultivar 'Beni Ryozhen'.
Depth of suture: Medium, elongated in suture plane. Average depth, 1.0 cm. Average diameter 0.5 cm, similar to cultivar 'Sordum'.
Bloom of skin: Strong, like cultivar 'Sordum'.
Ground color of skin: Yellowish green, classified in CIELab coordinates: L=46.29 a=−4.71 b=17.85 (Mcguire R. G., 1992), like cultivar 'Taiyou'.
Relative area of over color: Very large, like cultivar 'Friar'.
Over color of skin: Purple, classified in CIELab coordinates: L=535.14 a=127.76 b=53.44 (Mcguire R. G., 1992), like cultivar 'Karari'.
Pattern of over color: Solid flush only, similar to cultivar 'Friar'.
Number of lenticels: Medium, like cultivar 'Sunrise'.
Size of lenticels: Medium, like cultivar 'Extreme'.
Color of flesh: Yellowish green, the objective color in CIELab coordinates is L=631.83 a=−93.47 b=353.28 (Mcguire R. G., 1992), similar to cultivar 'Shiro'.
Firmness: Firm, reaching in average 7-8 pounds, like cultivar 'Laroda' and 'Taiyou'.
Juiciness: High, like cultivar 'Reubennel'.
Acidity: Low, reaching in average 1.1% malic acid when ripe, similar to cultivar 'Angeleno'.
Sweetness: High, reaching in average 20-22° Brix when ripe, like cultivar 'Black Gold'.
Aroma: Not detectable.
Adherence of stone to flesh: Non-adherent, similar to cultivar 'Fortune'.
Amount of fiber: Low.
Stone:
Size: Small, 1.8 cm long and 1.5 cm width, and 0.7 cm like cultivar 'Angeleno'.
Shape in lateral view: Medium elliptic, like cultivar 'Santa Rosa'.
Shape in ventral view: Medium elliptic, like cultivar 'Santa Rosa'.
Shape in basal view: Medium elliptic, like cultivar 'Bragialla'.
Symmetry in lateral view: Symmetric, similar to cultivar 'Angeleno'.
Texture of lateral surfaces: Granular, similar to cultivar 'Nubiana'.
Width of stalk-end: Medium, like cultivar 'Harry Pickstone'.
Additional stone information: In general the stone is particularly small compared with the whole fruit.
Pit cavity: It is as long and width as the pit, 2.0 cm long, 1.8 cm width, and 0.8 thickness. The color is brown in CIELab coordinates is L=29.82 a=3.76 b=12.33 (Mcguire R. G., 1992)
Kernel: The kernel is heart-shaped, brown color, in CIELab coordinates is L=50.62 a=10.79 b=21.10 (Mcguire R. G., 1992) and the length is 1.4 cm, the width 1.2 cm, and the thickness 0.5 cm.
Phenology:
Time of beginning of flowering: Very late, 2 weeks later than 'Angeleno'. In the Southern Hemisphere occurs between $10^{th}$ to $20^{th}$ September.
Time of beginning of fruit ripening: Very late, 3 weeks later than 'Angeleno'. In the Southern Hemisphere occurs between $10^{th}$ to $20^{th}$ March.
Keeping quality: After 60 days in cold storage +3 days at room temperature keeps a glossy flesh, good taste and crunchy flesh.
Shipping quality: After 60 days in cold storage +3 days at room temperature, the skin keeps the natural wax that inhibits from water loss, so the flesh is juicy and fresh. The flesh firmness ranges from 5 to 8 pounds and the soluble solids concentration remain high (18-21%). The variety is not susceptible to "chilling injury" and therefore can be suitable for exporting to distant markets from the production zone.

The invention claimed is:

1. A new and distinct plum tree substantially as illustrated and described.

* * * * *